United States Patent
Kojima et al.

(10) Patent No.: US 9,962,139 B2
(45) Date of Patent: May 8, 2018

(54) X-RAY IMAGE DIAGNOSTIC APPARATUS THAT ACQUIRES POSITION INFORMATION ASSOCIATED WITH A TABLE TOP

(71) Applicant: TOSHIBA MEDICAL SYSTEMS CORPORATION, Otawara-Shi (JP)

(72) Inventors: Tsuyoshi Kojima, Nasushiobara (JP); Toshiaki Kawano, Otawara (JP); Yoshinori Saito, Otawara (JP); Hisayasu Yumiza, Otawara (JP); Makoto Takanaka, Nasusshiobara (JP)

(73) Assignee: Toshiba Medical Systems Corporation, Otawara-Shi (JP)

( * ) Notice: Subject to any disclaimer, the term of this patent is extended or adjusted under 35 U.S.C. 154(b) by 260 days.

(21) Appl. No.: 14/633,465

(22) Filed: Feb. 27, 2015

(65) Prior Publication Data

US 2015/0250442 A1 Sep. 10, 2015

(30) Foreign Application Priority Data

Mar. 10, 2014 (JP) .................................. 2014-046830

(51) Int. Cl.
*A61B 6/00* (2006.01)
*A61B 6/04* (2006.01)

(52) U.S. Cl.
CPC ............ *A61B 6/547* (2013.01); *A61B 6/0457* (2013.01); *A61B 6/4233* (2013.01);
(Continued)

(58) Field of Classification Search
CPC ... A61B 6/0457; A61B 6/4233; A61B 6/4441; A61B 6/4464; A61B 6/4476; A61B 6/487; A61B 6/547
(Continued)

(56) References Cited

U.S. PATENT DOCUMENTS 5,901,199 A * 5/1999 Murphy .................. A61B 6/08 378/65
5,930,328 A 7/1999 Nakamura et al.
(Continued)

FOREIGN PATENT DOCUMENTS

JP 9-117442 5/1997
JP 2004-121604 4/2004
(Continued)

OTHER PUBLICATIONS

Japanese Office Action dated Nov. 14, 2017 in Japanese Application No. 2014-048830, 5 pages.

*Primary Examiner* — Allen C. Ho
(74) *Attorney, Agent, or Firm* — Oblon, McClelland, Maier & Neustadt, L.L.P.

(57) ABSTRACT

An X-ray image diagnostic apparatus is provided with an X-ray irradiation unit configured to perform irradiation with X-rays; a detection unit configured to detect the X-rays; a top table configured to be movable and allow a test object to be mounted; a position information acquisition unit configured to acquire first relative position information representing a relative position of the X-ray irradiation unit with respect to a position of the top table, and second relative position information representing a relative position of the detection unit with respect to the position of the top table, as clinical position information; and a drive control unit configured to drive the X-ray irradiation unit and the detection unit, based on displacement information representing a displacement of the position of the top table and the clinical position information.

12 Claims, 9 Drawing Sheets

(52) U.S. Cl.
CPC .......... *A61B 6/4441* (2013.01); *A61B 6/4464* (2013.01); *A61B 6/4476* (2013.01); *A61B 6/487* (2013.01); *A61B 6/545* (2013.01)

(58) Field of Classification Search
USPC .......................... 378/91, 196, 197, 205, 209
See application file for complete search history.

(56) References Cited

U.S. PATENT DOCUMENTS

| | | | | |
|---|---|---|---|---|
| 6,200,024 B1* | 3/2001 | Negrelli | ............ | A61B 6/4233 378/196 |
| 6,435,715 B1* | 8/2002 | Betz | ............ | A61B 6/4458 378/197 |
| 6,463,121 B1* | 10/2002 | Milnes | ............ | A61B 6/4482 378/62 |
| 6,516,046 B1 | 2/2003 | Fröhlich | ............ | A61B 6/04 378/205 |
| 6,619,839 B2* | 9/2003 | Yoshimura | ............ | A61B 6/0478 378/195 |
| 6,865,253 B2* | 3/2005 | Blumhofer | ............ | A61B 6/547 378/205 |
| 6,890,099 B2* | 5/2005 | Tanaka | ............ | A61B 6/08 378/197 |
| 6,893,157 B2* | 5/2005 | Arakawa | ............ | A61B 6/08 378/205 |
| 6,935,779 B2* | 8/2005 | Zhang | ............ | A61B 6/08 378/196 |
| 7,197,107 B2* | 3/2007 | Arai | ............ | A61B 6/032 378/15 |
| 7,204,640 B2* | 4/2007 | Fu | ............ | A61N 5/1049 378/205 |
| 7,246,943 B2* | 7/2007 | Gotoh | ............ | A61B 6/4014 378/196 |
| 7,401,977 B2* | 7/2008 | Graumann | ............ | A61B 6/4441 378/197 |
| 7,421,061 B2* | 9/2008 | Boese | ............ | A61B 5/721 378/205 |
| 7,453,984 B2* | 11/2008 | Chen | ............ | A61N 5/1049 378/65 |
| 7,478,949 B2* | 1/2009 | Niessen | ............ | A61B 6/08 378/197 |
| 7,488,107 B2* | 2/2009 | Tubbs | ............ | A61B 6/08 378/205 |
| 7,503,692 B2* | 3/2009 | De Godzinsky | ......... | A61B 6/08 378/205 |
| 7,503,693 B2* | 3/2009 | Jährling | ............ | G01T 1/02 378/205 |
| 7,522,701 B2* | 4/2009 | Jensen | ............ | A61B 6/481 378/162 |
| 7,572,057 B2* | 8/2009 | Takekoshi | ............ | A61B 6/4482 378/205 |
| 7,581,885 B2* | 9/2009 | Ertel | ............ | A61B 6/08 378/204 |
| 7,620,147 B2* | 11/2009 | Gertner | ............ | A61N 5/10 378/145 |
| 7,632,014 B2* | 12/2009 | Wolfe | ............ | A61B 6/4441 378/205 |
| 7,654,739 B2* | 2/2010 | Lumma | ............ | A61B 6/06 378/116 |
| 7,737,427 B2* | 6/2010 | Kito | ............ | A61B 6/4233 250/370.08 |
| 7,744,279 B2* | 6/2010 | Heath | ............ | A61B 6/08 378/196 |
| 7,894,649 B2* | 2/2011 | Fu | ............ | A61N 5/1049 378/65 |
| 7,916,835 B2* | 3/2011 | Abe | ............ | A61B 6/06 378/205 |
| 7,934,869 B2* | 5/2011 | Ivanov | ............ | A61N 5/1049 378/20 |
| 7,997,799 B2* | 8/2011 | Jabri | ............ | A61B 6/4035 378/154 |
| 8,174,358 B2* | 5/2012 | Butzine | ............ | A61B 6/544 340/12.22 |
| 8,313,238 B2* | 11/2012 | Takahashi | ............ | A61B 6/583 378/205 |
| 8,408,788 B2* | 4/2013 | Ozawa | ............ | A61B 6/102 378/197 |
| 8,690,426 B2* | 4/2014 | Liu | ............ | G03B 42/02 250/370.09 |
| 8,821,016 B2* | 9/2014 | Yang | ............ | A61B 6/4233 378/205 |
| 8,824,633 B2* | 9/2014 | Ohishi | ............ | A61B 6/4014 378/92 |
| 8,961,009 B2* | 2/2015 | Altvater | ............ | A61B 6/4441 378/197 |
| 9,028,144 B2* | 5/2015 | Choi | ............ | A61B 6/032 378/205 |
| 9,149,247 B2* | 10/2015 | Lee | ............ | A61B 6/4452 |
| 9,247,920 B2* | 2/2016 | Al Assad | ............ | A61B 6/5258 |
| 9,474,464 B2* | 10/2016 | Iwai | ............ | A61B 5/061 |
| 9,521,987 B2* | 12/2016 | Tajima | ............ | A61B 6/08 |
| 9,541,509 B2* | 1/2017 | Akahori | ............ | A61B 6/486 |
| 9,642,584 B2* | 5/2017 | Niebler | ............ | A61B 6/4441 |
| 9,668,706 B2* | 6/2017 | Kim | ............ | A61B 6/563 |

FOREIGN PATENT DOCUMENTS

| | | |
|---|---|---|
| JP | 2007-006913 A | 1/2007 |
| JP | 2012 125434 | 7/2012 |

* cited by examiner

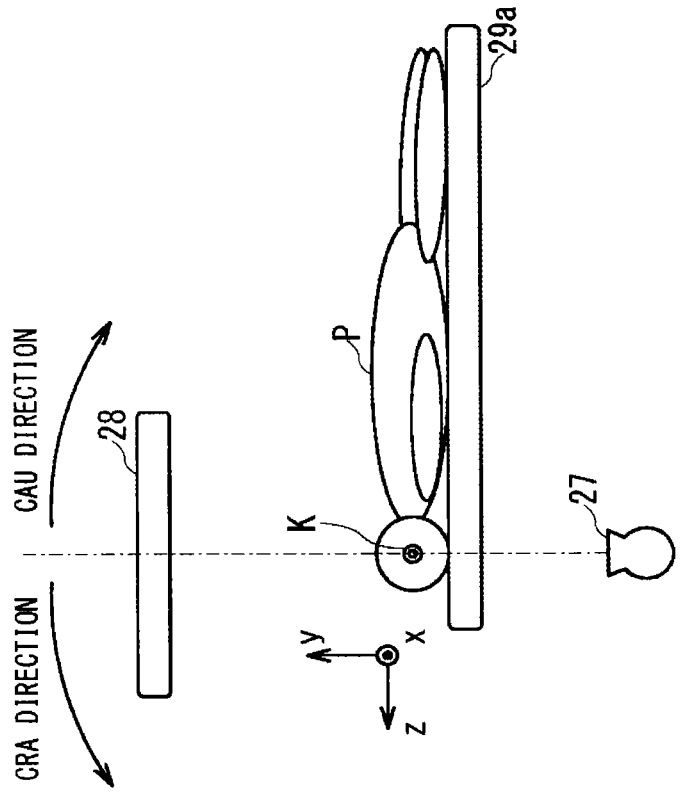
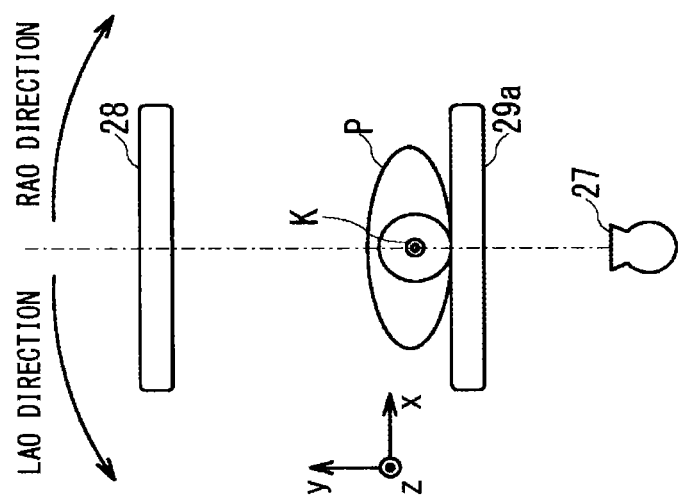
FIG. 6A
FIG. 6B

X-RAY IMAGE DIAGNOSTIC APPARATUS THAT ACQUIRES POSITION INFORMATION ASSOCIATED WITH A TABLE TOP

CROSS-REFERENCE TO RELATED APPLICATION

This application is based upon and claims the benefit of priority from Japanese Patent Application No. 2014-046830, filed on Mar. 10, 2014, the entire contents of which are incorporated herein by reference.

FIELD

Embodiments of the present invention relate to an X-ray image diagnostic apparatus.

BACKGROUND

In a patient image where a patient (test object) is taken, a coordinate system (also referred to as clinical angle coordinates) using a clinical angle as a coordinate system indicating the imaging direction is generally used.

The coordinate position indicated in the clinical angle coordinate system is determined on a side of a holding device, which includes an X-ray tube and an X-ray detector, as a positioning result by a drive shaft (movable shaft) of the holding device.

That is, a typical X-ray image diagnostic apparatus assumes a state where a bed position (top table position) is fixed. The apparatus determines a coordinate position in the clinical angle coordinate system according to the positioning result between the X-ray tube and the X-ray detector on the baths of drive control for the drive shaft (movable shaft) controlled on the side of the holding device.

Such a typical X-ray image diagnostic apparatus positions the apparatus only on the basis of drive control on the side of the holding device, and calculates the clinical angle coordinates as an angle for taking an image of a patient (test object) according to the positional relationship with the bed position (top table position) in a fixed state.

As described above, the clinical angle coordinates is thus calculated only on the basis of drive control for the drive shaft (movable shaft) of the holding device, which includes the X-ray tube and the X-ray detector. Conventionally, the bed position and the top table position, which include the patient to be imaged, are not considered at all.

Accordingly, the turning angle of the top table provided for the bed and the tilt angle of the top table are not reflected at all in the clinical angle coordinates calculated by the holding device. For instance, when a turning shaft (drive shaft) of the bed is driven to change the top table position and in turn change the turning angle of the top table and the tilt angle of the top table, the clinical angle coordinates calculated on the side of the holding device sometimes indicate an incorrect coordinate position.

To address this problem, an X-ray image diagnostic apparatus capable of calculating clinical angle coordinates that always indicate correct position and angle has been desired.

BRIEF DESCRIPTION OF THE DRAWINGS

In accompanying drawings,

FIGS. 6A and 6B are diagrams illustrating a clinical angle coordinates where the X-ray image diagnostic apparatus according to this embodiment replaces the center position in the coordinate system centered on the test object with the position of interest;

DETAILED DESCRIPTION

Figure 1:
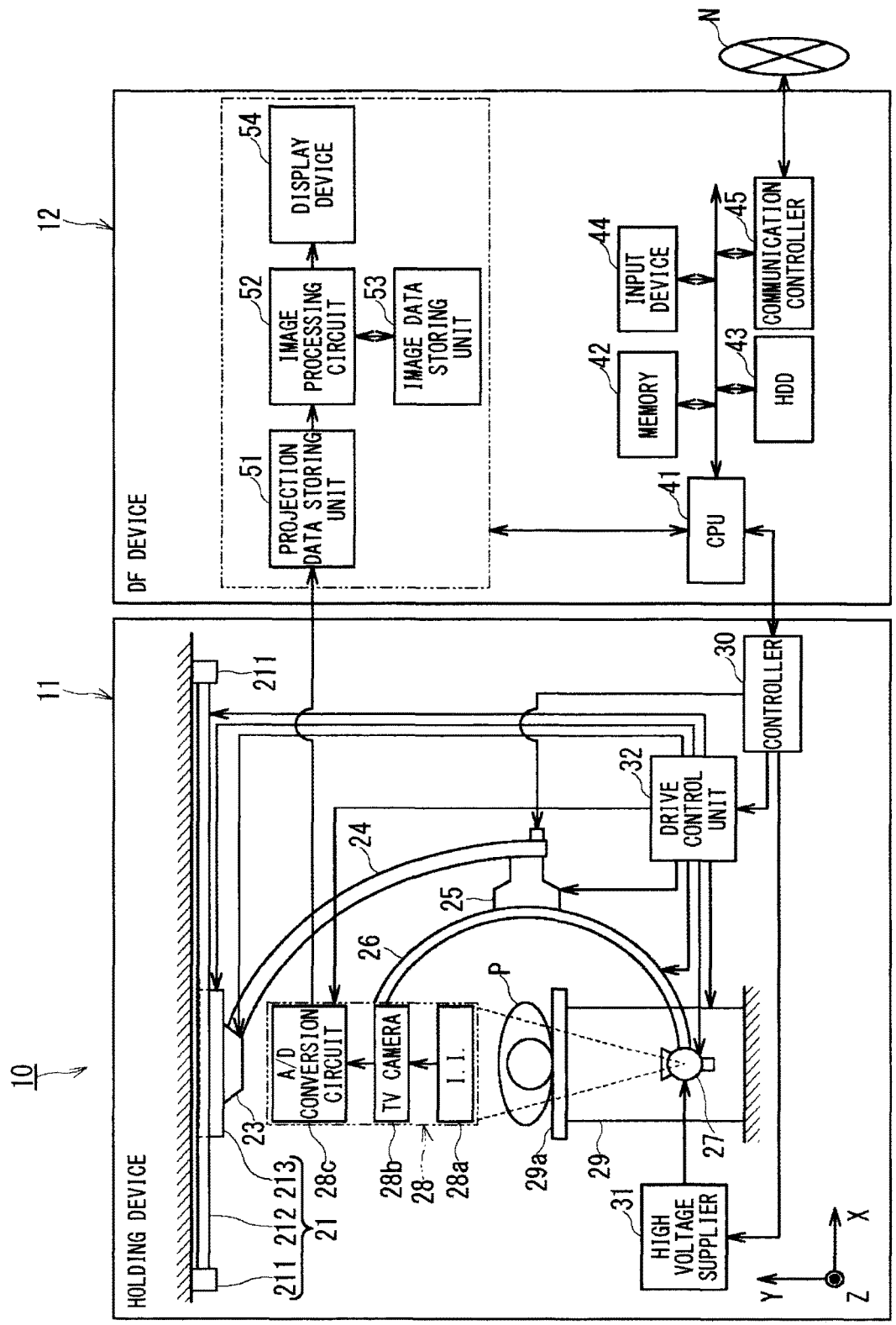
FIG. 1 is a schematic diagram showing a hardware configuration of an X-ray image diagnostic apparatus of this embodiment.

An X-ray image diagnostic apparatus according to this embodiment, comprises: an X-ray irradiation unit configured to perform irradiation with X-rays; a detection unit configured to detect the X-rays; a top table configured to be movable and allow a test object to be mounted; a position information acquisition unit configured to acquire first relative position information representing a relative position of the X-ray irradiation unit with respect to a position of the top table, and second relative position information representing a relative position of the detection unit with respect to the position of the top table, as clinical position information; and a drive control unit configured to drive the X-ray irradiation unit and the detection unit, based on displacement information representing a displacement of the position of the top table and the clinical position information.

An X-ray image diagnostic apparatus according to this embodiment comprises: an X-ray irradiation unit configured to perform irradiation with X-rays; a detection unit configured to detect the X-rays; a top table configured to be movable and allow a test object to be mounted; a top table position information acquisition unit configured to acquire position information on the top table; a calculation unit for a position of interest configured to acquire any of position information and angle information on the X-ray irradiation unit and the detection unit, and calculate the position of interest during irradiating the test object with the X-rays; a center coordinate conversion unit configured to replace a center position in a coordinate system centered on the test object with the calculated position of interest, based on at least any of the position information and angle information on the X-ray irradiation unit and the detection unit and a relative positional relationship with respect to the position information on the top table; an information correction unit configured to regard a displacement of the position information on the top table as a relative amount of movement from the replaced center position, and correct the position information or angle information on the X-ray irradiation unit and the detection unit; and a drive control unit configured to drive the X-ray irradiation unit and the detection unit, based on the corrected position information or angle information on the X-ray irradiation unit and the detection unit.

Accordingly, the X-ray image diagnostic apparatus according to this embodiment can take an image according to position information in a single coordinate system centered on the test object in consideration also of the position information on the top table when the clinical angle coordinates is used.

Furthermore, the X-ray image diagnostic apparatus according to this embodiment can take an image of the test object in consideration also of the position information on the top table. Accordingly, this apparatus can always calculate clinical angle coordinates representing the correct position and angle, and acquire taken image data having higher accuracy.

Before description of exemplary embodiments according to this embodiment, the problem is described with reference to the drawings in order to clarify the conventional problem.

Figure 9:
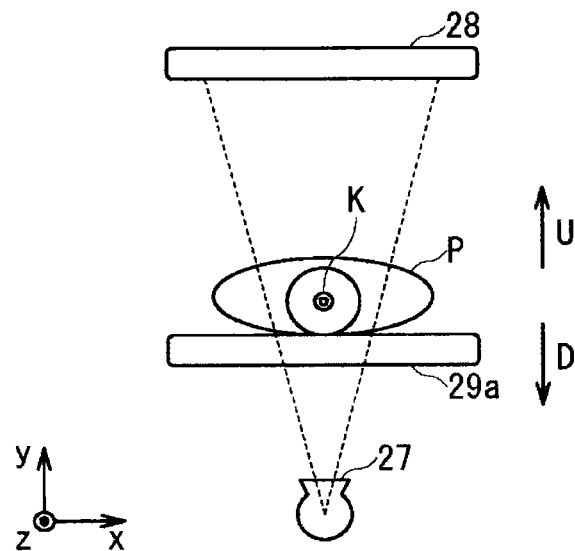
FIG. 9 is a diagram schematically illustrating a conventional X-ray image diagnostic apparatus where a test object mounted on a movable top table is irradiated with X-rays.

FIG. 9 is a diagram schematically illustrating a conventional X-ray image diagnostic apparatus where a test object P mounted on a movable top table 29a is irradiated with X-rays.

As shown in FIG. 9, the conventional X-ray image diagnostic apparatus takes an X-ray image through an X-ray irradiator 27 and a detector 28. A position of interest K is a position of interest where the test object P is irradiated with X-rays on the basis of position information about the X-ray irradiator 27 and the detector 28 and X-ray irradiation information.

The conventional X-ray image diagnostic apparatus calculates the clinical angle coordinates only from movement of the drive shaft (movable shaft) of the holding device, which holds the X-ray irradiator 27 and the detector 28, and acquires the position of interest K.

Accordingly, the conventional X-ray image diagnostic apparatus does not consider the position of the top table 29a and movement of the bed (not shown). Unfortunately, the apparatus cannot acquire a correct taken image in some cases of the positions of the top table 29a and the bed.

For instance, as shown in FIG. 9, even in a state where the test object P is fixed on the top table 29a, deviation of the position of the top table 29a in the upper direction U or the lower direction D deviates the position of interest K of the test object P. Accordingly, a correct taken image desired by a medical doctor and a medical technologist cannot be acquired.

Note that the bed is provided below the top table 29a. The bed includes drive shafts (movable shafts) for moving the top table 29a in vertical (front-back axis) and body axis (head-foot axis) directions and rotating this table in an X-Z plane.

Figure 10:
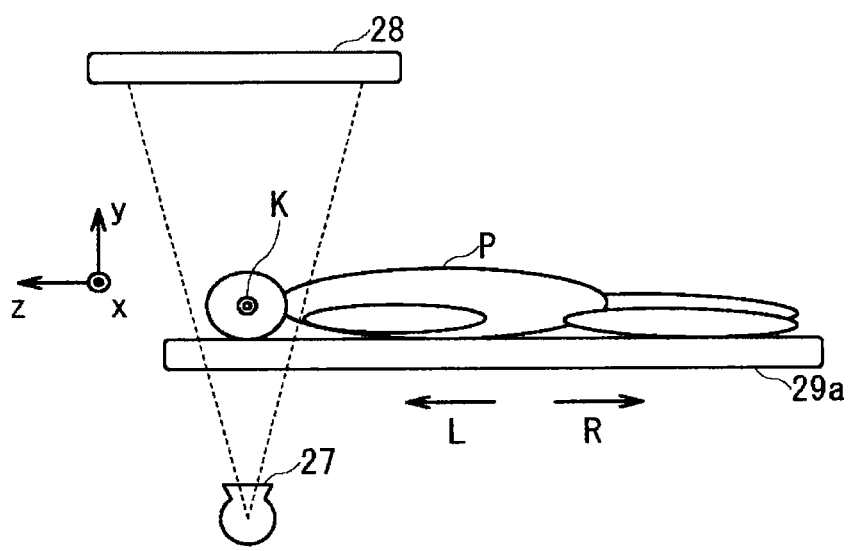
FIG. 10 is a diagram schematically illustrating, in side view, the conventional X-ray image diagnostic apparatus where the test object mounted on the top table is irradiated with X-rays.

FIG. 10 is a diagram schematically illustrating, in side view, the conventional X-ray image diagnostic apparatus where the test object P mounted on the top table 29a is irradiated with X-rays.

Likewise, in FIG. 10, an X-ray image is taken by the X-ray irradiator 27 and the detector 28. As with FIG. 9, the conventional X-ray image diagnostic apparatus calculates the clinical angle coordinates only from movement of the drive shaft (movable shaft) of the holding device, which holds the X-ray irradiator 27 and the detector 28. Accordingly, the apparatus does not consider the position of the top table 29a and movement of the bed, and cannot acquire a correct taken image in some cases of the positions of the top table 29a and the bed.

For instance, in the case of FIG. 10, deviation of the position of the top table 29a in the left direction L or the right direction R, in turn, deviates the position of interest K. Accordingly, a correct taken image desired by a medical doctor and a medical technologist cannot be acquired.

Figure 11:
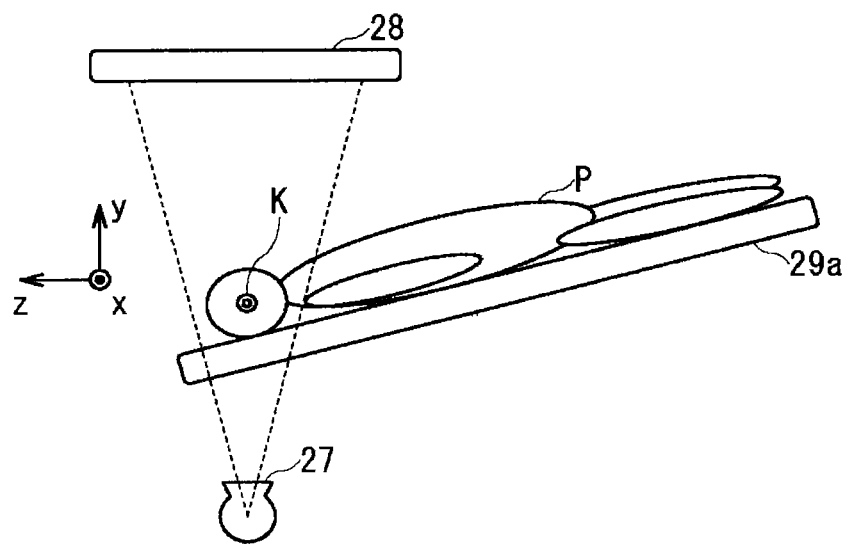
FIG. 11 is a diagram schematically illustrating, in side view, the conventional X-ray image diagnostic apparatus where the top table is tilted and the test object mounted on the top table is irradiated with X-rays.

FIG. 11 is a diagram schematically illustrating, in side view, the conventional X-ray image diagnostic apparatus where the top table 29a is tilted and the test object P mounted on the top table 29a is irradiated with X-rays.

Likewise, in FIG. 11, an X-ray image is taken by the X-ray irradiator 27 and the detector 28. In FIG. 11, even if the drive shaft (movable shaft) of the holding device holding the X-ray irradiator 27 and the detector 28 is fixed, the position of the top table 29a is in a state where the head side of the test object P (the left on the sheet) is lowered toward the X-ray irradiator 27 (after-mentioned longitudinal tilt). In a state where the position of the top table 29a is not considered, the medical doctor and the medical technologist perform an imaging operation.

That is, in the case of FIG. 11, deviation in position of head side of the test object P on the top table 29a in the direction toward the X-ray irradiator 27, in turn, vertically deviates the position of interest K. Accordingly, a correct taken image desired by the medical doctor and the medical technologist cannot be acquired.

Figure 12:
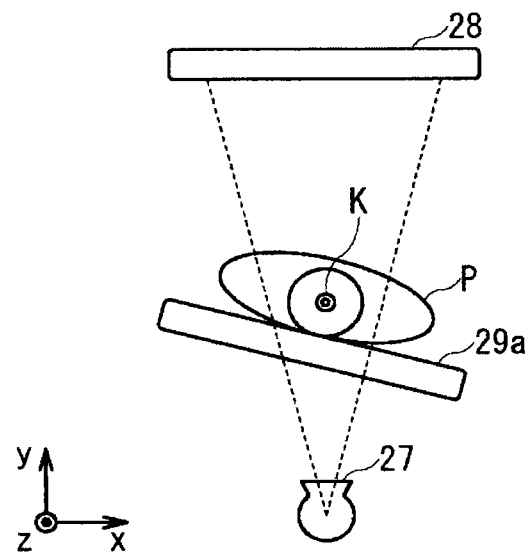
FIG. 12 is a diagram schematically illustrating the conventional X-ray image diagnostic apparatus where the test object mounted on the top table is irradiated with X-rays, in view in the direction from the parietal to the feet.

FIG. 12 is a diagram schematically illustrating the conventional X-ray image diagnostic apparatus where the test object P mounted on the top table 29a is irradiated with X-rays, in view in the direction from the parietal to the feet.

Likewise, in FIG. 12, an X-ray image is taken by the X-ray irradiator 27 and the detector 28. In FIG. 12, even if the drive shaft (movable shaft) of the holding device holding the X-ray irradiator 27 and the detector 28 is fixed, the position of the top table 29a is in a state where the right side (right side on the sheet) of the test object P is lowered (after-mentioned lateral tilt). In a state where the position of the top table 29a is not considered, the medical doctor and the medical technologist perform the imaging operation.

In the case of FIG. 12, the position of the top table 29a is turned to deviate clockwise centered on the body axis. Accordingly, the lateral orientation of the position of interest K deviates. A correct taken image desired by the medical doctor and the medical technologist cannot therefore be acquired.

As described above, in the conventional X-ray image diagnostic apparatus, for instance, the position of interest K deviates owing to parallel movement of the top table 29a in the y direction (FIG. 9), parallel movement of the top table 29a in the z direction (FIG. 10), turning in the yz plane (longitudinal tilt) (FIG. 11), turning in the xy plane (lateral tilt) (FIG. 12) and the like.

To address the problem, the X-ray image diagnostic apparatus according to this embodiment utilizes clinical angle control in a broad sense that acquires position information representing the position of the top table 29a and takes an image in consideration not only of the clinical angle coordinates but also of the position information about the top table 29a.

An X-ray image diagnostic apparatus according to this embodiment is hereinafter described with reference to the accompanying drawings.

Figure 2:
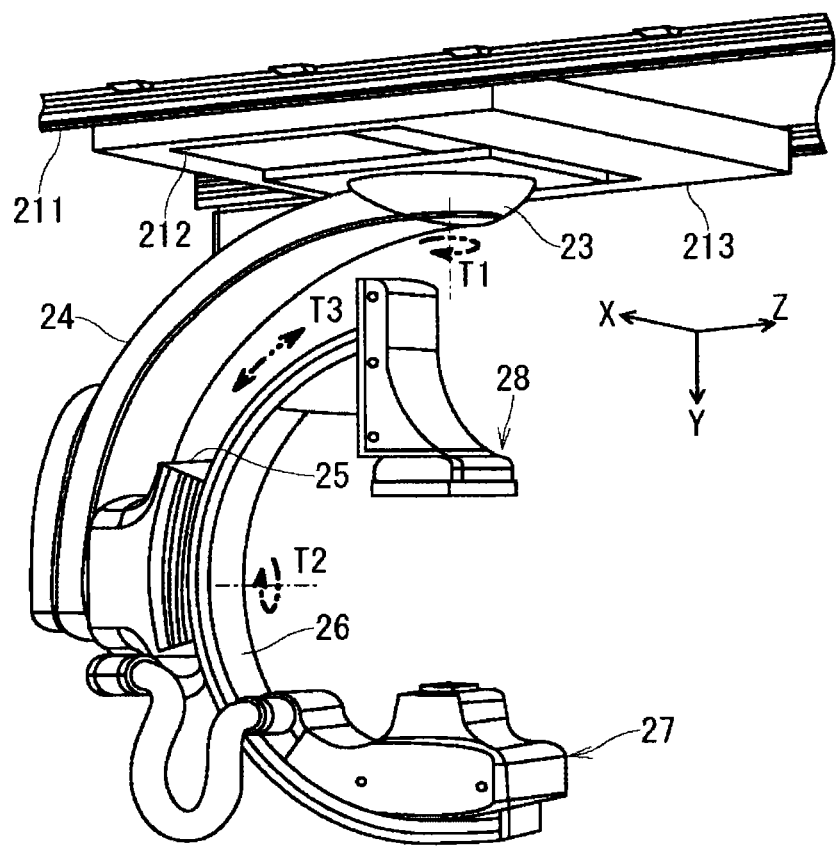
FIG. 2 is a perspective view showing an appearance of a holding device in the X-ray image diagnostic apparatus of this embodiment.

FIG. 1 is a schematic diagram showing a hardware configuration of an X-ray image diagnostic apparatus of this embodiment. FIG. 2 is a perspective view showing an appearance of a holding device in the X-ray image diagnostic apparatus of this embodiment.

FIGS. 1 and 2 show the X-ray image diagnostic apparatus 10 that includes a ceiling-traveling C-arm of this embodiment. The X-ray image diagnostic apparatus 10 roughly includes a holding device 11 and a DF (Digital Fluorography) device 12. The holding device 11 and the DF device 12 are typically installed in a laboratory and a treatment room.

The X-ray image diagnostic apparatus according to this embodiment is not limited to the X-ray image diagnostic apparatus 10 that includes the ceiling-traveling C-arm. Alternatively, this apparatus may be an X-ray image diagnostic apparatus that includes a floor-traveling C-arm, or an X-ray image diagnostic apparatus that includes a floor-standing C-arm. The description of this embodiment is made using an exemplary X-ray image diagnostic apparatus that includes a C-arm. However, the apparatus is not limited to this example. For instance, an X-ray irradiator and an X-ray detector may be held by respective arms independent of each other. Alternatively, the apparatus may be an X-ray image diagnostic apparatus that includes no C-arm.

The holding device 11 includes a sliding mechanism 21, a perpendicular axis turning mechanism 23, a suspension arm 24, a C-arm turning mechanism 25, a C-arm 26, an X-ray irradiator 27 (X-ray irradiation unit), a detector 28 (detection unit), a bed 29, a controller 30, a high voltage supplier 31, and a drive control unit 32.

The sliding mechanism 21 includes a Z-axis direction rail 211, an X-axis direction rail 212, and a vehicle 213. The sliding mechanism 21 is controlled by the controller 30 via the drive control unit 32 to slide the perpendicular axis turning mechanism 23, the suspension arm 24, the C-arm turning mechanism 25, the C-arm 26, the X-ray irradiator 27, and the detector 28 integrally in the horizontal direction.

The Z-axis direction rail 211 is arranged longitudinally in the Z-axis direction (the longitudinal axis direction of the top table 29a), and held on the ceiling.

The X-axis direction rail 212 is arranged in the X-axis direction (the lateral axis direction of the top table 29a), and held via rollers (not shown) at the opposite ends of this rail by the Z-axis direction rail 211. The X-axis direction rail 212 is controlled by the controller 30 via the drive control unit 32 to travel in the Z-axis direction on the Z-axis direction rail 211.

The vehicle 213 is held by the X-axis direction rail 212 via rollers (not shown). The vehicle 213 is controlled by the controller 30 via the drive control unit 32 to travel in the X-axis direction on the X-axis direction rail 212.

The X-axis direction rail 212 supporting the vehicle 213 is movable in the Z-axis direction on the Z-axis direction rail 211. The vehicle 213 is movable in the X-axis direction on the X-axis direction rail 212. Accordingly, the vehicle 213 is movable in the horizontal directions (X-axis and Z-axis directions) in the laboratory.

The perpendicular axis turning mechanism 23 is turnably supported by the vehicle 213. The perpendicular axis turning mechanism 23 is controlled by the controller 30 via the drive control unit 32 to turn the suspension arm 24, the C-arm turning mechanism 25, the C-arm 26, the X-ray irradiator 27 and the detector 28 integrally in a perpendicular axis turning direction T1 (shown in FIG. 2).

The suspension arm 24 is supported by the perpendicular axis turning mechanism 23.

The C-arm turning mechanism 25 is turnably supported by the suspension arm 24. The C-arm turning mechanism 25 is controlled by the controller 30 via the drive control unit 32 to turn the C-arm 26, the X-ray irradiator 27 and the detector 28 integrally in a turning direction T2 (show in FIG. 2) with respect to the suspension arm 24.

The C-arm 26 is supported by the C-arm turning mechanism 25, and allows the X-ray irradiator 27 and the detector 28 to be arranged opposite to each other centered on the test object P. The rear or a side surface of the C-arm 26 is provided with a rail (not shown). Through this rail sandwiched by the C-arm turning mechanism 25 and the C-arm 26, the C-arm 26 is controlled by the controller via the drive control unit 32 to move the X-ray irradiator 27 and the detector 28 integrally in an arc direction T3 (shown in FIG. 2) of the C-arm 26 along an arc locus.

The X-ray irradiator 27 is provided at one end of the C-arm 26. The X-ray irradiator 27 is arranged such that this irradiator can move to and fro under control of the controller 30 via the drive control unit 32. The X-ray irradiator 27 includes an X-ray tube. This irradiator is supplied with high voltage power by the high voltage supplier 31 to irradiate a prescribed portion of the test object P with X-rays according to the condition of the high voltage power. The X-ray irradiator 27 includes, on an X-ray emission side, an X-ray irradiation field stop that includes multiple lead blades, and a compensation filter that is made of silicone rubber for attenuating a predetermined amount of irradiation with X-rays so as to prevent halation. The X-ray irradiator 27 adjusts the X-ray irradiation field stop on the basis of irradiation information about irradiation with X-rays, and identifies the position of interest of the test object P during irradiating the test object P with X-rays.

The detector 28 is provided at the other end of the C-arm 26 on the emission side of the X-ray irradiator 27. The detector 28 is arranged such that this detector can move to and fro under control of the controller 30 via the drive control unit 32. The detector 28, which is an I.I. (Image Intensifier)-TV system, roughly includes an I.I. 28a, a TV camera 28b, and an A/D (Analog to Digital) conversion circuit 28c. The I.I. 28a converts X-rays having passed through the test object P or directly incident X-rays into visible light, and multiplies the brightness through a process of light-electrons-light conversion to form projection data having a high sensitivity. The TV camera 28b includes a CCD (Charge Coupled. Device) image pickup element, which converts the optical projection data into an electric signal. The A/D conversion circuit 28c converts a time-series analog signal (video signal) output from the TV camera 28b into a digital signal.

The detector 28 may include a flat panel detector (FPD). If the detector 28 includes the FPD, the detector causes a two-dimensionally arranged detection elements to detect X-rays and convert the X-rays into an electric signal. It is thus sufficient that the detector 28 can only detect the X-rays having passed through the test object P or directly incident X-rays.

The X-ray irradiator 27 and the detector 28 are arranged opposite to each other as a pair by the C-arm 26. However, according to this embodiment, the number of pairs is not limited to one. Thus, two or more pairs of the X-ray irradiators 27 and detectors 28 may be adopted.

The bed 29 is supported on the floor and, in turn, supports the top table (catheter table) 29a. The bed 29 is controlled by the controller 30 via the drive control unit 32 to move the top table 29a horizontally (in the X and Z-axes directions) and vertically (Y-axis direction) and roll this table. The top table 29a allows the test object P to be mounted on this table, and is movable. The case of an under-tube type holding device 11 where the X-ray irradiator 27 is disposed below the top table 29a is described. Alternatively, this device may be an over-tube type holding device where the X-ray irradiator 27 is disposed above the top table 29a. Furthermore, a configuration may be adopted where an X-ray image diagnostic apparatus with no C-arm causes the bed 29 to drive the top table 29a.

The controller 30 includes a CPU (Central Processing Unit), not shown, and a memory. The controller 30 controls operations of the high voltage supplier 31, the drive control unit 32 and the like. The controller 30 controls the drive control unit 32, which drives the bed 29 and the top table 29a. This control can calculate position information representing the position of the bed 29 and position information representing the position of the top table 29a.

The high voltage supplier 31 can supply the X-ray irradiator 27 with high voltage power according to control by the controller 30.

The drive control unit 32 can drive each of the sliding mechanism 21, the perpendicular axis turning mechanism 23, the C-arm turning mechanism 25, the C-arm 26, the X-ray irradiator 27, the detector 28, and the top table 29a of the bed 29, according to control by the controller 30.

The DF device 12 has a computer-based configuration, and can mutually communicate with a network N, such as a hospital backbone LAN (Local Area Network). The DF device 12 comprises hardware that roughly includes a CPU 41 as a processor, a memory 42, a HDD (Hard Disc Drive) 43, an input device 44, a communication controller 45, a projection data storing unit 51, an image processing circuit 52, an image data storing unit 53, and a display device 54. The CPU 41 is mutually connected to each of hardware configuration elements configuring the DF device 12 via a bus as a common signal transmission path. In some cases, the DF device 12 includes a drive (not shown) for a recording medium.

When an operator, such as a medical doctor or a medical technologist, operates the input device 44 to input an instruction, the CPU 41 executes a program stored in the memory 42. Alternatively, the CPU 41 loads, onto the memory 42, a program stored in a HDD 43, a program transferred from the network N, received by the communication controller 45 and installed in the HDD 43, or a program read from a recording medium inserted in a drive (not shown) for the recording medium and installed in the HDD 43, and then executes the program.

The memory 42 is a storing device having a configuration that includes elements both of ROM (Read Only Memory) and RAM (Random Access Memory). The memory 42 stores data on IPL (Initial Program Loading) and BIOS (Basic Input/Output System), and used as working memory of the CPU 41 and for temporarily storing data.

The HDD 43 is a storing device having a configuration internally and undetachably including a metallic HD (Hard Disk) on which magnetic material is applied or vapor-deposited. The HDD 43 stores a program (including not only an application program but also an OS (Operating System)) installed in the DF device 12, and data. The OS may provide GUI (Graphical User Interface) that heavily uses graphics for displaying information for a tester and allows basic operations to be performed through the input device 44.

The input device 44 may be a keyboard, a mouse and the like that can be operated by an operator. Input signals according to operations are transmitted to the CPU 41. The input device 44 roughly includes a main console and a system console.

The communication controller 45 performs communication control according to standards. The communication controller 45 has a function capable of connection with the network N via a telephone line. The DF device 12 can be connected to the network N via the communication controller 45.

The projection data storing unit 51 is controlled by the CPU 41 to store projection data output from the A/D conversion circuit 28c of the holding device 11.

The image processing circuit 52 is controlled by the CPU 41 to apply a logarithmic transformation process (LOG process) to the projection data stored in the projection data storing unit 51, and perform an adding process as necessary, thereby generating data on a fluoroscopic image and a taken image (DA (Digital Angiography) image). The image processing circuit 52 applies image processing to the fluoroscopic image and the taken image stored in the image data storing unit 53. The image processing includes processes of enlarging, shading and spatially filtering data, processes of minimum-value-tracing and maximum-value-tracing data accumulated in time series, and an adding process for removing noise. Data having subjected to the image processing by the image processing circuit 52 is output to the display device 54 while being stored in a storing device, such as the image data storing unit 53.

The image data storing unit 53 is controlled by the CPU 41 to store, as data, the fluoroscopic image and the taken image output from the image processing circuit 52.

The display device 54 is controlled by the CPU 41 to superimpose test information (character information on parameters, a scale, etc.), such as a patient name, on data about the fluoroscopic image and the taken image generated by the image processing circuit 52, D/A (Digital to Analog) converts the combined signal, and subsequently displays the signal as a video signal. The display device 54 may be a live monitor that displays live the fluoroscopic image and the taken image output from the image processing circuit 52, a reference monitor that displays the taken image output from the image processing circuit 52 as a still image or plays back a moving image, and a system monitor that displays data for principally controlling the holding device 11, such as data for switching FOV (Field Of View).

Figure 3:
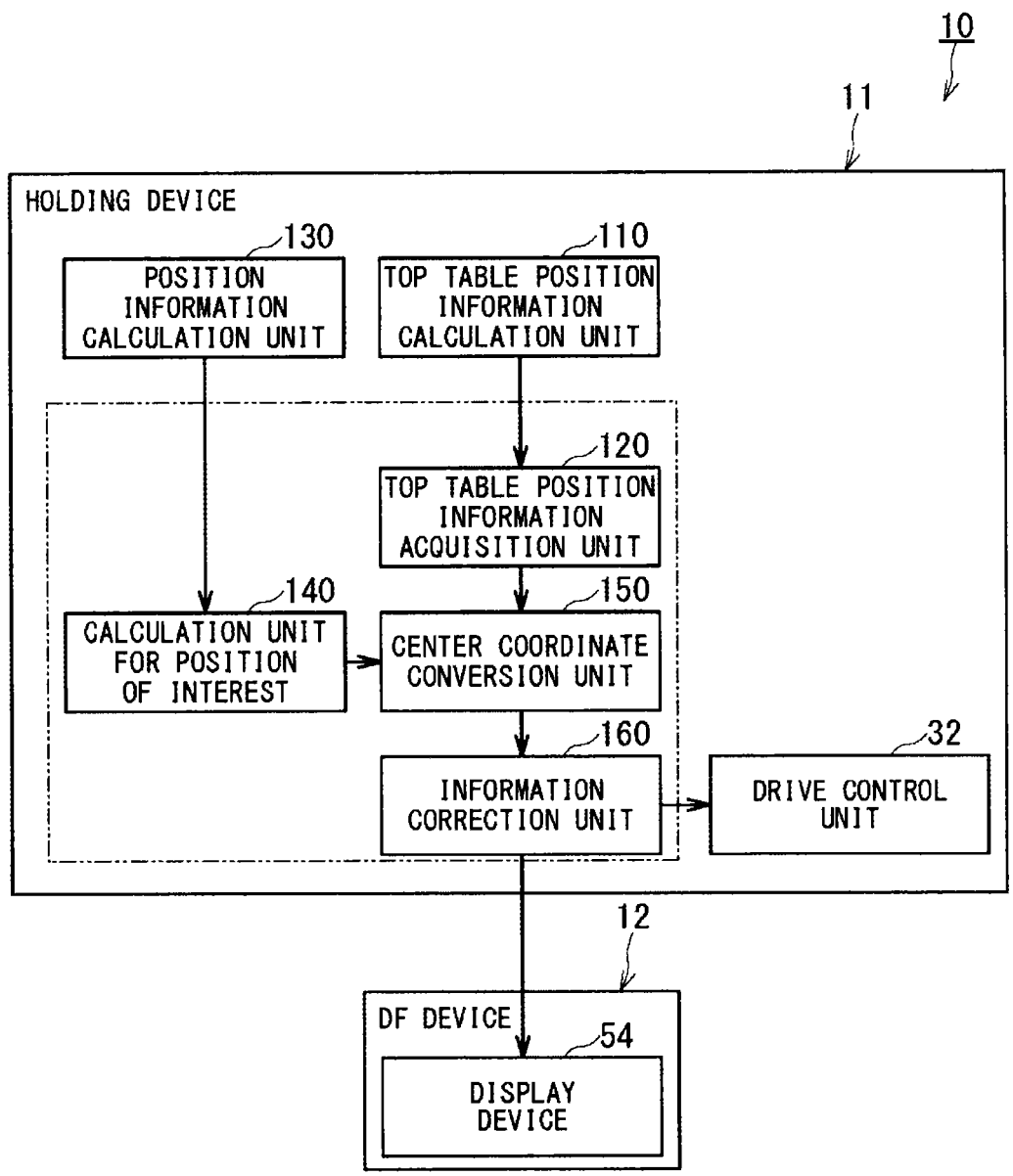
FIG. 3 is a block diagram showing a function of the X-ray image diagnostic apparatus of this embodiment.

FIG. 3 is a block diagram showing a function of the X-ray image diagnostic apparatus of this embodiment.

The controller 30 (or CPU 41) shown in FIG. 1 executes the program to allow the X-ray image diagnostic apparatus 10 (FIG. 1) to function as a top table position information calculation unit 110, a top table position information acquisition unit 120, a position information calculation unit 130, a calculation unit 140 for a position of interest, a center coordinate conversion unit 150, an information correction unit 160, the drive control unit 32, and the display device 54, as shown in FIG. 3. The description is made using the example where the elements 110 to 160 and the drive control unit 32 are provided as functions of the X-ray image diagnostic apparatus 10 for the holding device 11. All or some of the elements 110 to 160 and the drive control unit 32 may be provided as hardware for the X-ray image diagnostic apparatus 10. The display device 54 is included in the DF device 12.

The top table position information calculation unit 110 calculates the position information on the top table 29*a*. For instance, for allowing the controller 30 to control the drive control unit 32, the top table position information calculation unit 110 can calculate the movement position (or position information) of the bed 29 and the position information on the top table 29*a*.

The top table position information acquisition unit 120 acquires the position information on the top table 29*a* from the top table position information calculation unit 110.

The position information calculation unit 130 calculates at least any of the position information on the X-ray irradiator 27, angle information on the X-ray irradiator 27, position information on the detector 28, and angle information on the detector 28. For instance, for allowing the controller 30 to control the drive control unit 32, the position information calculation unit 130 calculates the position information on the X-ray irradiator 27, and the position information on the detector 28. The position information calculation unit 130 may calculate the angle information on the X-ray irradiator 27, and the angle information on the detector 28.

The calculation unit 140 for a position of interest can acquire at least any of the position information on the X-ray irradiator 27, the angle information on the X-ray irradiator 27, the position information on the detector 28 and the angle information on the detector 28, and calculate the position of interest, calculated on position information calculation unit 130, for irradiating the test object P with X-rays.

The top table position information acquisition unit 120 and the calculation unit 140 for a position of interest may configure a position information acquisition unit. For instance, the position information acquisition unit, which includes the top table position information acquisition unit 120 and the calculation unit 140 for a position of interest, can acquire first relative position information representing the relative position of the X-ray irradiator 27 with respect to the position of the top table 29*a*, and second relative position information representing the relative position of the detector 28 with respect to the position of the top table 29*a*, as clinical position information.

The first relative position information and the second relative position information can be represented by coordinates. Likewise, the clinical position information can represented by coordinates.

The center coordinate conversion unit 150 replaces the center position in the coordinate system centered on the test object P with the position of interest calculated by the calculation unit 140 for position of interest, on the basis of a relative positional relationship between any of the position information on the X-ray irradiator 27, the angle information on the X-ray irradiator 27, the position information on the detector 28 and the angle information on the detector 28, and the position information on the top table 29*a*.

The information correction unit 160 regards the displacement in position information on the top table 29*a* as the relative amount of movement in the replaced coordinate system centered on the test object P, and corrects the position information on the X-ray irradiator 27, the angle information on the X-ray irradiator 27, the position information on the detector 28, or the angle information on the detector 28. The information representing the displacement in position of the top table 29*a* is also referred to as displacement information.

The drive control unit 32 (see FIG. 1) drives the X-ray irradiator 27 and the detector 28, based on any of the corrected pieces of information including the position information on the X-ray irradiator 27, angle information on the X-ray irradiator 27, position information on the detector 28 and angle information on the detector 28.

The drive control unit 32 can drive the X-ray irradiator 27 and the detector 28 on the basis of, for instance, the displacement information representing the displacement in position of the top table 29*a* and clinical position information.

The display device 54 (see FIG. 1) displays the corrected center position in the coordinate system centered on the test object P by information correction unit 160 as clinical angle coordinates.

As described above, the X-ray image diagnostic apparatus 10 according to this embodiment acquires the position information on the top table 29*a*, calculates the position of interest for irradiating the test object P with X-rays, and replaces the center position in the coordinate system centered on the test object P with the calculated position of interest, on the basis of the relative positional relationship between any of the position information on the X-ray irradiator 27, the angle information on the X-ray irradiator 27, the position information on the detector 28 and the angle information on the detector 28, and the position information on the top table 29*a*.

Accordingly, the X-ray image diagnostic apparatus 10 according to this embodiment can regard the displacement in position information on the top table 29*a* as the relative amount of movement from the center position in the replaced coordinate system centered on the test object P, and correct the position information on the X-ray irradiator 27, the angle information on the X-ray irradiator 27, the position information on the detector 28, or the angle information on the detector 28.

The information correction unit 160 can correct the center position in the coordinate system centered on the test object P every time when correcting the displacement in position information on the top table 29*a* as the relative amount of movement. This correction allows an image to be taken on the basis of the position information in a single coordinate system centered on the test object in consideration also of the position information on the top table every time when using the clinical angle coordinates. Each of the pieces of position information and displacement information can represent positions in coordinates.

A correcting method performed by the X-ray image diagnostic apparatus 10 according to this embodiment is hereinafter described with reference to two examples.

The X-ray image diagnostic apparatus 10 according to this embodiment takes images of the test object P at various angles in some cases. Accordingly, the apparatus sometimes performs an operation of tilting the top table 29*a*. Thus, in this embodiment, the operation of tilting the top table 29*a* is referred to as tilt. In this embodiment, an operation of tilting the longitudinal axis of the top table 29*a* is referred to as longitudinal tilt (see FIG. 11), and an operation of tilting the lateral axis of the top table 29*a* is referred to as lateral tilt (see FIG. 12).

(First Correcting Method)

For instance, a correcting method in the case where a top table 29a deviates by lateral movement is described with reference to the drawings.

Figure 4:
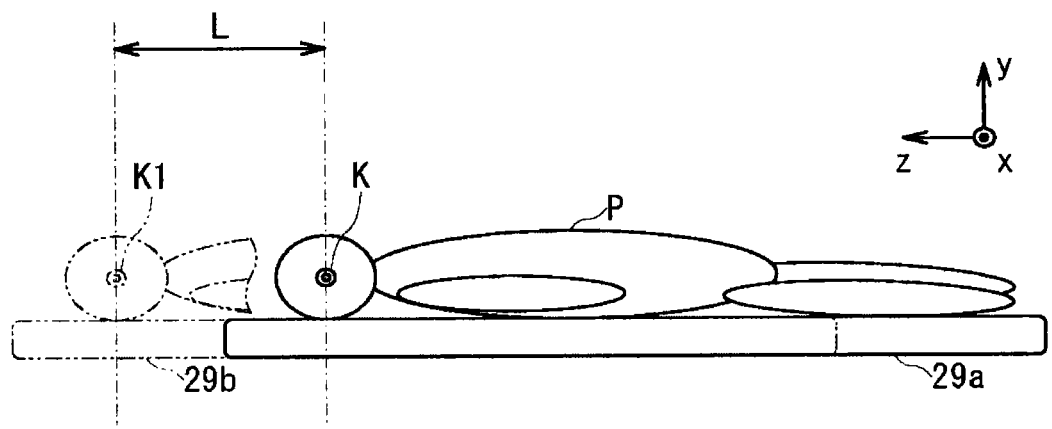
FIG. 4 is a diagram illustrating a concept where an X-ray image diagnostic apparatus according to this embodiment regards the displacement in position information on a top table as the relative amount of movement from the center position (position of interest) in a coordinate system centered on a test object and corrects the position information on an X-ray irradiator and a detector.

FIG. 4 is a diagram illustrating a concept where an X-ray image diagnostic apparatus 10 according to this embodiment regards the displacement in position information on a top table 29a as the relative amount of movement from the center position (position of interest K) in a coordinate system centered on a test object P and corrects the position information on an X-ray irradiator 27 and a detector 28.

In the diagram of FIG. 4, the test object P is mounted on the top table 29a. The X-ray image diagnostic apparatus 10 according to this embodiment acquires position information on the X-ray irradiator 27 and the detector 28, and calculates the position of interest K for irradiating the test object P with X-rays.

The X-ray image diagnostic apparatus 10 according to this embodiment includes the center coordinate conversion unit 150, which replaces the center position in the coordinate system centered on the test object P with the position of interest K on the basis of the relative positional relationship between the position information on the X-ray irradiator 27 and the detector 28, and the position information on the top table 29a.

It is here assumed that the top table 29a is moved by a distance L in the left direction on the sheet (Z-axis direction) in a state where the test object P is mounted. In this case, it is assumed that the top table 29a moves to a top table 29b. The X-ray image diagnostic apparatus 10 according to this embodiment can cause the top table position information calculation unit 110 to acquire the position information on the top table 29b. Accordingly, this apparatus can acquire displacement (i.e., displacement information) in position information from the top table 29a to the top table 29b.

The X-ray image diagnostic apparatus 10 according to this embodiment includes the information correction unit 160, which can regard the displacement in position information to the top table 29b as the relative amount of movement from the center position (position of interest K) in the coordinate system centered on the test object P and correct the position information on the X-ray irradiator 27 and the detector 28. That is, the information correction unit 160 may calculate the relative amount of movement on the basis of the displacement information representing the displacement from the top table 29a to the top table 29b, and correct the position information on the X-ray irradiator 27 and the detector 28.

In this case, the position of interest K1 on the top table 29b is displaced by a distance L from the position of interest K on the top table 29a. Accordingly, the position information on the X-ray irradiator 27 and the detector 28 has a difference by the distance L from the top table 29b. Thus, the information correction unit 160 of the X-ray image diagnostic apparatus 10 according to this embodiment regards the position information on the X-ray irradiator 27 and the detector 28 as the relative amount of movement, and corrects the difference in distance L. The drive control unit 32 drives the X-ray irradiator 27 and the detector 28 on the basis of the corrected position information on the X-ray irradiator 27 and the detector 28.

Thus, the X-ray image diagnostic apparatus 10 according to this embodiment can correct the position information on the X-ray irradiator 27 and the detector 28 to the position of interest K1 for irradiation with X-rays. Accordingly, this apparatus can take an image on the basis of the position information in the single coordinate system centered on the test object P in consideration of the position information on the top table 29b.

Furthermore, the X-ray image diagnostic apparatus 10 according to this embodiment can take an image of the test object P in consideration of the position information on the top table 29b. Accordingly, this apparatus can acquire taken image data (taken image) having higher accuracy.

(Second Correcting Method)

Next, for instance, a correcting method in the case where a top table 29a is tilted is described with reference to the drawings.

Figure 5:
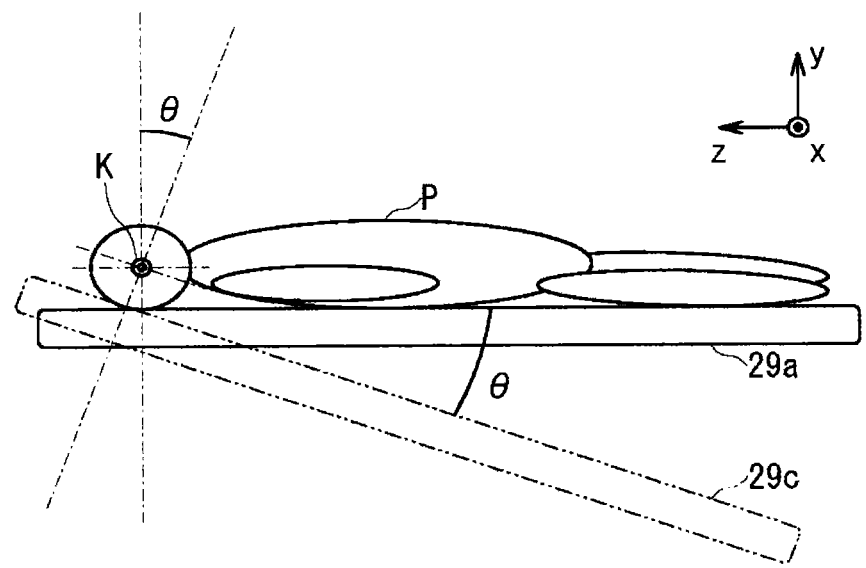
FIG. 5 is a diagram illustrating a concept where an X-ray image diagnostic apparatus according to this embodiment regards the displacement in position information on a top table as the relative amount of movement from the center position (position of interest K) in a coordinate system centered on a test object and corrects the angle information on an X-ray irradiator and a detector.

FIG. 5 is a diagram illustrating a concept where an X-ray image diagnostic apparatus 10 according to this embodiment regards the displacement in position information on a top table 29a as the relative amount of movement from the center position (position of interest K) in a coordinate system centered on a test object P and corrects the angle information on an X-ray irradiator 27 and a detector 28.

In the diagram of FIG. 5, the test object P is mounted on the top table 29a. The X-ray image diagnostic apparatus 10 according to this embodiment acquires angle information on the X-ray irradiator 27 and the detector 28 with respect to the top table 29a, and calculates the position of interest K for irradiating the test object P with X-rays.

The X-ray image diagnostic apparatus 10 according to this embodiment includes the center coordinate conversion unit 150, which replaces the center position in the coordinate system centered on the test object P with the position of interest K on the basis of the relative positional relationship between the angle information on the X-ray irradiator 27 and the detector 28 and the position information on the top table 29a.

It is here assumed that the top table 29a is moved by an angle CAU (Caudal) θ (degree), which will be described later, in the lower direction on the sheet in a state where the test object P is mounted. In this case, for instance, it is assumed that the top table 29a is moved to a top table 29c by an angle of 30 degrees (i.e., the longitudinal tilt).

The X-ray image diagnostic apparatus 10 according to this embodiment can cause the top table position information calculation unit 110 to acquire the position information on the top table 29c. Accordingly, upon detection of the longitudinal tilt, this apparatus can acquire the displacement in position information from the top table 29a to the top table 29c.

The X-ray image diagnostic apparatus 10 according to this embodiment includes the information correction unit 160, which can regard the displacement in position information to the top table 29c as the relative amount of movement from the center position (position of interest K) in the coordinate system centered on the test object P and correct the angle information on the X-ray irradiator 27 and the detector 28.

In this case, the top table 29c has the angle of CAU 30 (degrees) from the top table 29a. Accordingly, the angle information on the X-ray irradiator 27 and the detector 28 has a difference by CRA (Cranial) 30 (degrees) from the top table 29c. Thus, the information correction unit 160 of the X-ray image diagnostic apparatus 10 according to this embodiment regards the angle information on the X-ray irradiator 27 and the detector 28 as the relative amount of movement, and corrects CAU 30 (degrees).

Thus, the X-ray image diagnostic apparatus 10 according to this embodiment can correct the angle information on the X-ray irradiator 27 and the detector 28 to the same position as the position of interest K for irradiation with X-rays.

Accordingly, this apparatus can take an image on the basis of the position information in the single coordinate system centered on the test object P in consideration of the angle information on the top table 29c.

Furthermore, the X-ray image diagnostic apparatus 10 according to this embodiment can take an image of the test object P in consideration of the angle information on the top table 29c. Accordingly, this apparatus can acquire taken image data (taken image) having higher accuracy.

Next, three examples are provided, and each example is described in detail.

Example 1: Clinical Angle Control Operation

An X-ray image diagnostic apparatus 10 according to this exemplary embodiment acquires position information on a top table 29a. Here, displacements in position information (i.e., displacement information) on the top table 29a can be roughly classified into an amount of movement according to movement of the top table 29a, an amount of movement according to turning movement of the top table 29a, and an amount of movement according to the tilt of the top table 29a during imaging a test object P.

Therefore, displacement information representing the displacement of the top table 29a may be any of the amount of movement according to the tilt of the top table 29a, the amount of movement according to movement of the top table 29a, and the amount of movement according to the turning movement of the top table 29a during imaging the test object P.

The X-ray image diagnostic apparatus 10 according to this embodiment causes a controller 30 to control a drive control unit 32 even with any amount of movement of the top table 29a. Accordingly, this apparatus can calculate the position information after movement.

For instance, the X-ray image diagnostic apparatus 10 according to this embodiment, as Example 1, can correct the position information on the X-ray irradiator 27, the angle information on the X-ray irradiator 27, the position information on the detector 28, or the angle information on the detector 28 so as to relatively cancel the displacement in position information on the top table 29a, and adopt the corrected information, which is position information on the X-ray irradiator 27, the angle information on the X-ray irradiator 27, the position information on the detector 28 or the angle information on the detector 28, as the center position in the coordinate system centered on the test object P.

FIGS. 6A and 6B are diagrams illustrating a clinical angle coordinates where the X-ray image diagnostic apparatus 10 according to this embodiment replaces the center position in the coordinate system centered on the test object P with the position of interest K.

The center coordinate conversion unit 150 (FIG. 3) according to this embodiment replaces the center position in the coordinate system centered on the test object P with the position of interest K on the basis of the relative positional relationship between the position of interest K during irradiating the test object P with X-rays and the position information on the top table 29a. The information correction unit 160 regards the displacement in position information on the top table 29a as the relative amount of movement from the center position (position of interest K) in the coordinate system centered on the test object P, and corrects the position information on the X-ray irradiator 27, the angle information on the X-ray irradiator 27, the position information on the detector 28, or the angle information on the detector 28.

Here, in FIGS. 6A and 6B, for instance, according to the corrected angle information on the X-ray irradiator 27 and the detector 28 described with reference to FIG. 5, the position of interest K is displayed as the center position in the coordinate system centered on the test object P represented in the clinical angle coordinates.

That is, in FIG. 6B, the angle information on the X-ray irradiator 27 and the detector 28 is thus corrected. For instance, through use of the difference of CRA 30 (degrees), the angle information on the X-ray irradiator 27 and the detector 28 is corrected by CAU 30 (degree), The corrected clinical angle coordinates are displayed as the center position (reference) in the coordinate system centered on the test object P.

As shown in FIG. 6A, in this embodiment, the turning direction in which the X-ray irradiator 27 and the detector 28 are turned by the C-arm 26 (FIG. 2) during irradiating the test object P is represented.

For instance, FIG. 6A is a view in parallel to the body axis of the test object P from the head to the feet of the test object P. The turning angle in the clockwise direction (clockwise direction on the sheet) around the longitudinal direction (body axis direction) of the test object P is referred to as RAO (Right Anterior Oblique). The turning angle in the counterclockwise direction (counterclockwise direction on the sheet) around the longitudinal direction (body axis direction) of the test object P is referred to as LAO (Left Anterior Oblique).

That is, when the C-arm 26 (FIG. 2) moves in the T2 direction (FIG. 2), the counterclockwise direction of the test object P is referred to as the LAO direction, and the clockwise direction is referred to as the RAO direction.

FIG. 6B shows a view from the right to the left of the test object P in FIG. 6A. The turning angle in the head direction (counterclockwise direction on the sheet) around the lateral direction of the test object P is referred to as CRA. The turning angle in the feet direction (clockwise direction on the sheet) around the lateral direction of the test object P is referred to as CAU.

That is, when the C-arm 26 (FIG. 2) moves in the T3 direction (FIG. 2), the head direction of the test object P is referred to as a CRA direction, and the feet direction is referred to as a CAU direction.

The position of the C-arm 26 with respect to the test object P can be represented by assigning angles by which the C-arm 26 is turned in the RAO, LAO, CRA and CAU directions. For instance, the position can be represented as RAO 10 (degrees), CAU 10 (degrees), LAO 20 (degrees), CRA 20 (degrees) and the like.

The X-ray image diagnostic apparatus 10 according to this embodiment can represent, in clinical angle coordinates, the center position (position of interest K) in the coordinate system centered on the test object P, according to the corrected pieces of information including the position information on the X-ray irradiator 27, the angle information on the X-ray irradiator 27, the position information on the detector 28 and the angle information on the detector 28. The angles are assigned with reference to the corrected clinical angle coordinates, and display and imaging can be performed.

Accordingly, the X-ray image diagnostic apparatus 10 according to this embodiment can calculate the position information on the top table 29a described in the prior art in FIGS. 9 to 12, and assign angles representing clinical angle coordinates and perform display in a state where the deviation in position information on the top table 29a shown in FIGS. 9 to 12 is respectively corrected as the relative amount of movement.

Furthermore, the X-ray image diagnostic apparatus 10 according to this embodiment can successively calculate (calculate in real time) the position information on the top table 29a. Accordingly, even if the angles in the clinical angle coordinate system is changed or even if the position information on the top table 29a varies, the displacement in position information on the top table 29a can be corrected on each time of the change and variation.

The X-ray image diagnostic apparatus 10 according to this embodiment can thus correct the position information into clinical angle coordinates in the coordinate system of the center position of the test object P in consideration of the drive shaft (movable shaft) of the bed 29 (FIG. 1) and the longitudinal tilt and lateral tilt of the top table 29a.

Thus, even when the operator changes the angles (CRA/CAU, LAO/RAO) of the position of interest K of the test object P desired to be taken images using the input device 44, correction can be made that regards the displacement in position information on the top table 29a as the relative amount of movement from the center position of the test object P to thereby perform clinical angle control in a state where the position of interest K is always the center position.

As described above, in Example 1, the X-ray image diagnostic apparatus 10 according to this embodiment can correct the position information on the X-ray irradiator 27, the angle information on the X-ray irradiator 27, the position information on the detector 28, or the angle information on the detector 28 so as to relatively cancel the displacement in position information on the top table 29a, and adopt the corrected information, which is position information on the X-ray irradiator 27, the angle information on the X-ray irradiator 27, the position information on the detector 28 or the angle information on the detector 28, as the center position in the coordinate system centered on the test object P.

Accordingly, the X-ray image diagnostic apparatus 10 according to this embodiment can take an image at the position of interest K of the test object P in a state where the position of interest K of the test object P is spatially fixed.

Example 2: Detector-Facing Correcting Operation

Next, in consideration of the amount of movement according to the turning movement of the top table 29a as the displacement in position information on the top table 29a, a method of correcting the amount of movement according to the turning movement of the X-ray detector is described. The basic configuration is the same as that of Example 1. Only movement of the top table 29a to be corrected is different.

FIGS. 7A to 7D are diagrams illustrating a correcting operation facing an X-ray detector that includes an X-ray irradiator 27 and a detector 28; this operation is also referred to simply as an X-ray detector-facing correcting operation.

In FIGS. 7A to 7D, the X-ray irradiator 27 and the detector 28 face with each other by means of a C-arm 26. Accordingly, if the top table 29a is viewed from the top, the X-ray irradiator 27 is disposed immediately below the detector 28. Thus, with reference to the C-arm 26 and the detector 28, the X-ray detector-facing correcting operation is described.

Figure 7A:
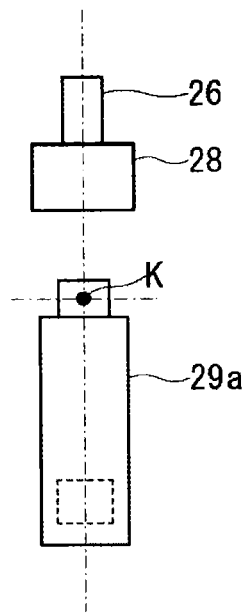
FIGS. 7A to 7D are diagrams illustrating a correcting operation facing an X-ray detector that includes an X-ray irradiator and a detector; this operation is also referred to simply as an X-ray detector-facing correcting operation.

FIG. 7A shows that, provided that a test object is mounted on the top table 29a, fixation of the top table 29a, in turn, fixes the position of interest K of the test object.

Figure 7B:
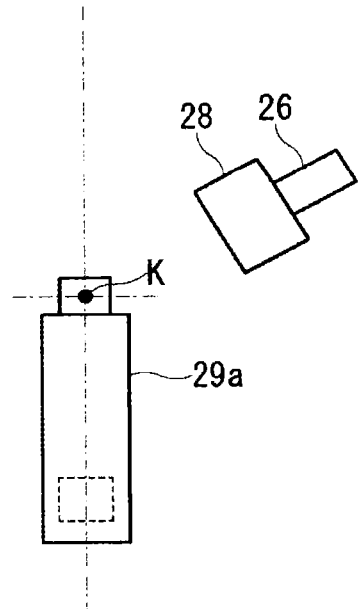

FIG. 7B is a diagram showing a state where the C-arm 26 and, the detector 28 move centered on the position of interest K of the test object P for an imaging operation. The C-arm 26 includes a turning mechanism and an expansion and contraction mechanism. Accordingly, turning imaging can be performed centered on the position of interest K of the test object in a state where the relative positional relationship with the position of interest K of the test object is maintained.

Figure 7C:
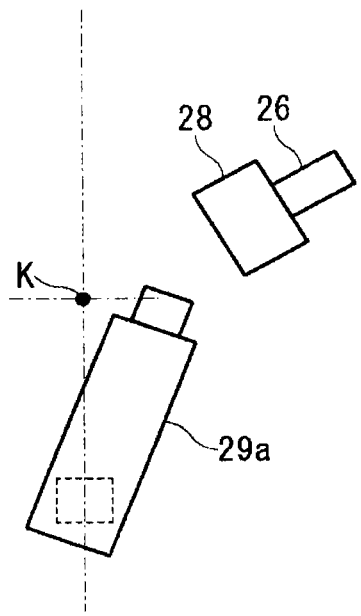

FIG. 7C shows a state where only the top table 29a turns according to the turning shaft (drive shaft) of the bed 29 from the state of the position in FIG. 7B. In typical imaging, for instance, when the parietal of the test object is desired to be taken, turning imaging is performed according to an instruction by a medical doctor and a medical technologist in a state where the position of interest K is fixed.

However, when turning imaging is performed by means of the C-arm 26, the top table 29a is sometimes required to be moved by the turning shaft (drive shaft) of the bed 29 in order to take an image of the parietal of the test object. In this case, the position of interest K of the test object mounted on the top table 29a should be moved according to the turning movement of the top table 29a. Unfortunately, the conventional X-ray image diagnostic apparatus cannot factor in (consider) the displacement in position of the top table 29a by means of the turning shaft (drive shaft) of the bed 29.

To address this problem, the X-ray image diagnostic apparatus 10 according to this embodiment acquires the position information on the top table 29a in FIG. 7A or 7B, and converts the position of interest K on the test object into the center position of the coordinate system centered on the test object on the basis of the relative positional relationship between the point of interest K of the test object and the position information on the top table 29a.

Figure 7D:
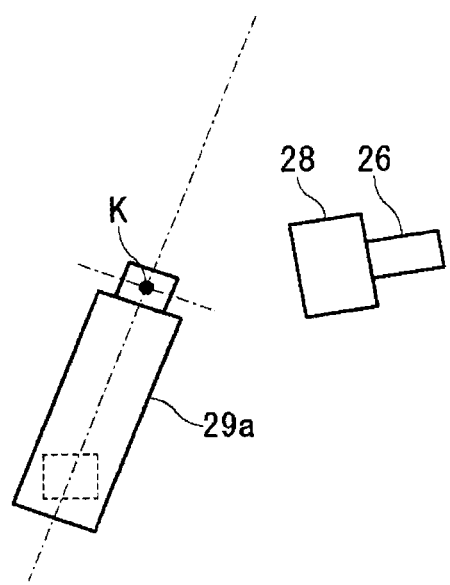

In FIG. 7D, the X-ray image diagnostic apparatus 10 according to this embodiment regards the displacement in position information on the top table 29a by means of the turning shaft (drive shaft) of the bed 29 (FIG. 7C) as, for instance, the relative amount of movement from the position of interest K in FIG. 7B, and corrects the position information on the X-ray irradiator 27 and the detector 28.

As described above, the X-ray image diagnostic apparatus 10 according to this embodiment can cause the position of interest K of the test object to coincide with the center position in the coordinate system centered on the test object. Accordingly, the X-ray image diagnostic apparatus 10 according to this embodiment can always acquire a taken image in correct clinical angle coordinates irrespective of the turning angle of the turning shaft (drive shaft) of the bed 29.

Example 3: Insertion Direction Instructing Operation (Auto Positioning Operation)

The X-ray image diagnostic apparatus 10 according to this embodiment has a function of an insertion direction instructing operation (auto positioning operation.

The insertion direction instructing operation (auto positioning operation) is a function where any position of the C-arm 26 holding the X-ray irradiator 27 and the detector 28 or of the holding device 11 is associated with a certain number, the position is preliminarily registered, and at the time of testing, an operator such as a medical doctor or a medical technologist inputs the number in conformity with the test to allow the C-arm 26 and the holding device 11 to automatically moved to and be arranged at the position associated with the number.

FIGS. 8A to 8D are diagrams illustrating the insertion direction instructing operation (auto positioning operation) of the X-ray image diagnostic apparatus 10 according to this embodiment, in this exemplary embodiment.

Figure 8A:
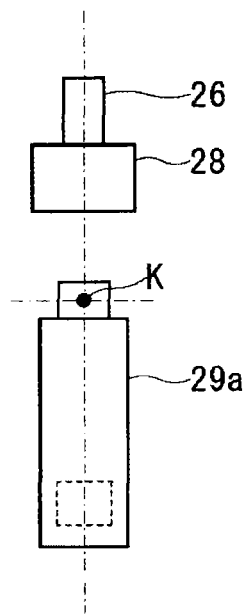
FIGS. 8A to 8D are diagrams illustrating the insertion direction instructing operation (auto positioning operation) of the X-ray image diagnostic apparatus according to this embodiment, in this exemplary embodiment.

FIG. 8A shows an arrangement in the case where the X-ray irradiator 27 and the detector 28 face each other by means of the C-arm 26, and the top table 29a is viewed from the top. If the top table 29a is viewed from the top, the X-ray irradiator 27 is disposed immediately below the detector 28. Accordingly, the insertion direction instructing operation (auto positioning operation) is described with respect to the C-arm 26 and the detector 28.

As described in FIG. 8A, in the case where the test object is mounted on the top table 29a, fixation of the top table 29a, in turn, fixes the position of interest K of the test object by means of the C-arm 26 provided with the X-ray irradiator 27 and the detector 28.

Figure 8B:
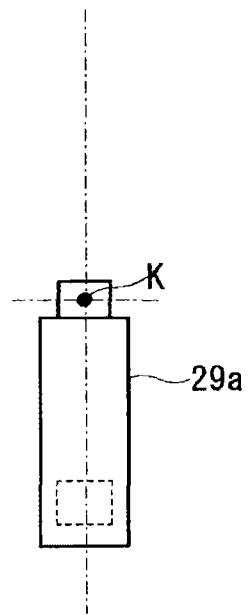

FIG. 8B is a diagram illustrating a state where the C-arm 26 and the detector 28 temporarily move centered on the position of interest K of the test object during an imaging operation. It is assumed that, in Example 3, the position information on the C-arm 26 and the holding device 11 is held by the insertion direction instructing operation (auto positioning operation).

Figure 8C:
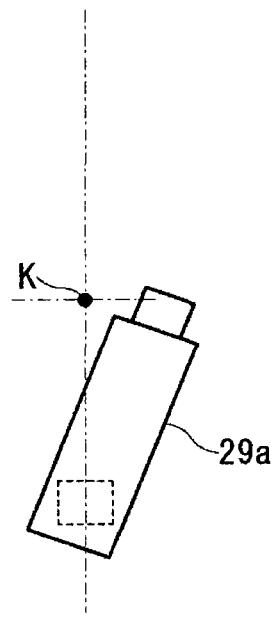

FIG. 8C shows that the position of the top table 29a deviates with respect to, for instance, an operation position of the medical doctor and the medical technologist when the insertion direction instructing operation (auto positioning operation) returns the C-arm 26, the holding device 11 and the like to predetermined positions. The top table 29a can be moved by the bed 29. Alternatively, the position of the top table 29a may be freely moved without being limited to automatic or manual movement.

The position of interest K of the test object shown in FIG. 8C is different from the positions according to the positions of the top table 29a in FIGS. 8A and 8B because the medical doctor and the medical technologist cause the positions of the top table 29a to deviate.

Figure 8D:
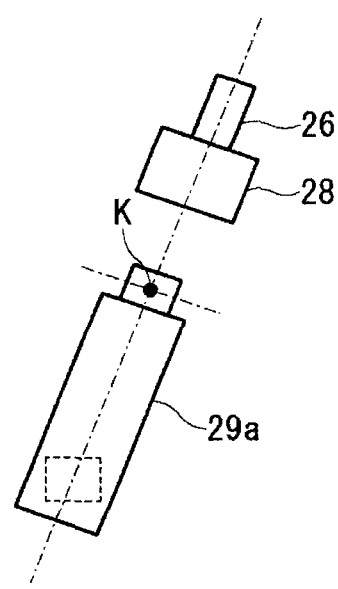

FIG. 8D shows a mode where the insertion direction instructing operation (auto positioning operation) returns the positions of the C-arm 26 and the holding device 11 to the original positions.

For instance, in FIGS. 8A and 8B, the X-ray image diagnostic apparatus 10 according to this embodiment causes the center coordinate conversion unit 150 to replace the center position in the coordinate system centered on the test object with the position of interest K on the basis of the relative positional relationship between the position information on the X-ray irradiator 27 and the detector 28 and the position information on the top table 29a.

In FIG. 8D, the X-ray image diagnostic apparatus 10 according to this embodiment can cause the information correction unit 160 to regard the displacement in position information on the top table 29a as the relative amount of movement from the center position (position of interest K) in the coordinate system centered on the test object and correct the position information on the X-ray irradiator 27 and the detector 28.

The X-ray image diagnostic apparatus 10 according to this embodiment can cause the information correction unit 160 to maintain the relative positional relationship between the X-ray irradiator 27 and the detector 28, and the top table 29a, and regard the displacement in position information on the top table 29a as the relative amount of movement from the center position (position of interest K) in the coordinate system centered on the test object and correct the position information on the X-ray irradiator 27 and the detector 28.

Accordingly, the apparatus can achieve a restoration operation function through the insertion direction instructing operation (auto positioning operation).

As described above, the X-ray image diagnostic apparatus 10 according to this embodiment can acquire the position information on the top table 29a, convert the position of interest into the center position in the coordinate system centered on the test object on the basis of the relative positional relationship between the position of interest and the position information on the top table 29a during irradiating the test object with X-rays, and perform correction while regarding the displacement in position information on the top table 29a as the relative amount of movement from the center position in the coordinate system centered on the test object.

Furthermore, the X-ray image diagnostic apparatus 10 according to this embodiment exemplified in Examples 1 to 0.3 can acquire taken image data (taken image) on the basis of correct position information in the coordinate system centered on the test object P while displaying the data in the single coordinate system. Accordingly, the apparatus can improve use efficiency and improve usability while improving maneuver efficiency.

Moreover, even if the position of the bed 29 or the top table 29a deviates during maneuver, various control operations can be performed in consideration of (factoring in) the deviation in position of the bed 29 or the top table 29a. Accordingly, correct and secure maneuver can be maintained.

As described above, the X-ray image diagnostic apparatus 10 according to this embodiment causes the center coordinate conversion unit 150 to replace the center position in the coordinate system centered on the test object P with the position of interest K.

For instance, the X-ray image diagnostic apparatus 10 according to this embodiment may provide the center coordinate conversion unit (posture setting unit) 150 with a function of setting the sleep posture (a sleep position) defined by the head position or feet position of the test object P. For example, the sleep posture refers to the attitude determination of the test object P on the top table 29a.

The attitude determination is intended to indicate there is the test object P's head-to-head side of the top table 29a, or on the head side of the top table 29a whether there is the test object P's foot. In other words, the attitude determination is intended to indicate there is the test object P's head to the foot side of the table 29a or the foot side of the top table 29a to whether there is the test object P's foot.

In this case, the center coordinate conversion unit 150 can replace the center position in the coordinate system centered on the test object P with the position of interest K calculated by the calculation unit 140 for the position of interest, factoring in the posture information on the top table 29a defined by the sleep posture.

Accordingly, the drive control unit 32 of the X-ray image diagnostic apparatus 10 according to this embodiment can drive the X-ray irradiator 27 and the detector 28 on the basis of the set posture information on the posture of the test object P and the clinical position information.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray image diagnostic apparatus, comprising:
an X-ray source configured to perform irradiation with X-rays;
a radiation detector configured to detect the X-rays;
a top table configured to be movable and allow a test object to be mounted; and
processing circuitry configured to:
acquire first relative position information representing a relative position of the X-ray source with respect to a position of the top table and second relative position information representing a relative position of the radiation detector with respect to the position of the top table, as clinical position information, and
drive the X-ray source and the radiation detector, based on displacement information representing a displacement of the position of the top table and the clinical position information, and set a posture defined by a head position or a feet position of the test object,
wherein the processing circuitry is further configured to drive the X-ray source and the radiation detector based on set posture information representing the posture and the clinical position information.

2. The X-ray image diagnostic apparatus according to claim 1, further comprising
an arm configured to hold the X-ray source and the radiation detector, wherein
the processing circuitry is further configured to:
calculate a position of interest during irradiating the test object on the top table with the X-rays, based on at least one of position information on the X-ray source, angle information on the X-ray source, position information on the radiation detector, and angle information on the radiation detector, and
drive the arm so as to maintain a position relationship between a relative position of the X-ray source with respect to the position of interest and a relative position of the radiation detector with respect to the position of interest.

3. The X-ray image diagnostic apparatus according to claim 1, wherein the first relative position information, the second relative position information, and the position of the top table are represented in coordinates.

4. An X-ray image diagnostic apparatus comprising:
an X-ray source configured to perform irradiation with X-rays;
a radiation detector configured to detect the X-rays;
a top table configured to be movable and allow a test object to be mounted; and
processing circuitry configured to:
acquire first relative position information representing a relative position of the X-ray source with respect to a position of the top table, and second relative position information representing a relative position of the radiation detector with respect to the position of the top table, as clinical position information, and
drive the X-ray source and the radiation detector, based on displacement information representing a displacement of the position of the top table and the clinical position information, wherein
the displacement information representing the displacement in position of the top table is any of an amount of movement according to tilt of the position of the top table during taking an image of the test object, an amount of movement according to movement of the top table, and an amount of movement according to turning movement of the top table.

5. The X-ray image diagnostic apparatus according to claim 4, further comprising
an arm configured to hold the X-ray source and the radiation detector,
wherein the processing circuitry is further configured to:
calculate a position of interest during irradiating the test object on the top table with the X-rays, based on at least one of position information on the X-ray source, angle information on the X-ray source, position information on the radiation detector, and angle information on the radiation detector, and
drive the arm so as to maintain position relationship between a relative position of the X-ray source with respect to the position of interest and a relative position of the radiation detector with respect to the position of interest.

6. The X-ray image diagnostic apparatus according to claim 4, wherein the first relative position information, the second relative position information, and the position of the top table are represented in coordinates.

7. An X-ray image diagnostic apparatus, comprising:
an X-ray source configured to perform irradiation with X-rays;
a radiation detector configured to detect the X-rays;
a top table configured to be movable and allow a test object to be mounted; and
processing circuitry configured to:
acquire position information on the top table, acquire any of position information on the X-ray source, angle information on the X-ray source, position information on the radiation detector, and angle information on the radiation detector, and calculate a position of interest during irradiating the test object with the X-rays,
replace a center position in a coordinate system centered on the test object with the calculated position of interest, based on at least one of the position information on the X-ray source, the angle information on the X-ray source, the position information on the radiation detector, and the angle information on the radiation detector,
regard a displacement of the position information on the top table as a relative amount of movement from the replaced center position, and correct any of the position information on the X-ray source, the angle information on the X-ray source, the position information on the radiation detector, and the angle information on the radiation detector, and
drive the X-ray source and the radiation detector, based on the position information on the X-ray source, the angle information on the X-ray source, the position information on the radiation detector, and the angle information on the radiation detector which have been corrected.

8. The X-ray image diagnostic apparatus according to claim 7, wherein the displacement in position information on the top table is an amount of movement according to movement of the position of the top table or an amount of movement according to turning movement of the top table during taking an image of the test object.

9. The X-ray image diagnostic apparatus according to claim 7, wherein the displacement in position information on the top table is an amount of movement according to tilt of the position of the top table during taking an image of the test object.

10. The X-ray image diagnostic apparatus according to claim 7, further comprising
   a bed that supports the top table, wherein
   the processing circuitry is further configured to:
      calculate a movement position of the bed, and
      calculate the position information on the top table from the movement position of the bed.

11. The X-ray image diagnostic apparatus according to claim 7, wherein the processing circuitry is further configured to:
   regard the displacement in the position information on the top table as the relative amount of movement from the replaced center position, and
   correct any of the position information on the X-ray source, the angle information on the X-ray source, the position information on the radiation detector, and the angle information on the radiation detector, based on the position information on the X-ray source and the position information on the radiation detector, and a relative positional relationship with respect to the position information on the top table.

12. The X-ray image diagnostic apparatus according to claim 7, further comprising
   a display device configured to display the center position in the coordinate system centered on the test object, wherein
   the processing circuitry is further configured to:
      cause the display device to display clinical angle coordinates based on the position information on the X-ray source, the angle information on the X-ray source, the position information on the radiation detector, and the angle information on the radiation detector, which have been corrected, every time when correcting any of the position information on the X-ray source, the angle information on the X-ray source, the position information on the radiation detector, and the angle information on the radiation detector, which are the relative amount of movement.

\* \* \* \* \*